(12) United States Patent
Imamoto et al.

(10) Patent No.: US 11,498,935 B2
(45) Date of Patent: Nov. 15, 2022

(54) OPTICALLY ACTIVE BISPHOSPHINOMETHANE, METHOD FOR PRODUCING THE SAME, AND TRANSITION METAL COMPLEX AND ASYMMETRIC CATALYST

(71) Applicant: NIPPON CHEMICAL INDUSTRIAL CO., LTD., Tokyo (JP)

(72) Inventors: Tsuneo Imamoto, Tokyo (JP); Ken Tamura, Tokyo (JP); Natsuhiro Sano, Tokyo (JP)

(73) Assignee: NIPPON CHEMICAL INDUSTRIAL CO., LTD., Tokyo (JP)

( * ) Notice: Subject to any disclaimer, the term of this patent is extended or adjusted under 35 U.S.C. 154(b) by 0 days.

(21) Appl. No.: 17/620,233

(22) PCT Filed: Jun. 9, 2020

(86) PCT No.: PCT/JP2020/022667
§ 371 (c)(1),
(2) Date: Dec. 17, 2021

(87) PCT Pub. No.: WO2020/261974
PCT Pub. Date: Dec. 30, 2020

(65) Prior Publication Data
US 2022/0204537 A1    Jun. 30, 2022

(30) Foreign Application Priority Data

Jun. 24, 2019   (JP) .............................. JP2019-116410

(51) Int. Cl.
*C07F 9/50* (2006.01)
*B01J 31/24* (2006.01)
*C07B 53/00* (2006.01)

(52) U.S. Cl.
CPC ......... *C07F 9/5004* (2013.01); *B01J 31/2414* (2013.01); *C07B 53/00* (2013.01)

(58) Field of Classification Search
None
See application file for complete search history.

(56) References Cited

U.S. PATENT DOCUMENTS

| 6,194,593 B1 | 2/2001 | Imamoto et al. |
| 2007/0021610 A1 | 1/2007 | Imamoto et al. |

FOREIGN PATENT DOCUMENTS

| CA | 2 287 713 A1 | 4/2000 |
| JP | 2000-136193 A | 5/2000 |
| JP | 2000-319288 A | 11/2000 |
| JP | 2007-56007 A | 3/2007 |
| JP | 2008-189610 A | 8/2008 |
| JP | 2008-189633 A | 8/2008 |
| JP | 2010-209008 A | 9/2010 |
| WO | 2005/087370 A1 | 9/2005 |

OTHER PUBLICATIONS

Sawatsugawa et al. "A Bulky Three-Hindered Quadrant Bisphosphine Ligand: Synthesis and Application in Rhodium-Catalyzed Asymmetric Hydrogenation of Functionalized Alkenes" Organic Letters, 2019, vol. 21, pp. 8874-8878.*
International Search Report dated Aug. 18, 2020, issued in counterpart International Application No. PCT/JP2020/022667 (2 pages).
Decision to Grant a Patent dated Sep. 14, 2021, issued in counterpart JP Patent Application No. 2019-116410, w/English translation (6 pages).

* cited by examiner

*Primary Examiner* — Joseph R Kosack
(74) *Attorney, Agent, or Firm* — WHDA, LLP

(57) ABSTRACT

There is provided a novel optically active bisphosphinomethane useful as a ligand for an asymmetric catalyst, excellent in oxidation resistance in air, and easy in handling. There is also provided a transition metal complex using the optically active bisphosphinoraethane having excellent asymmetric catalytic ability as a ligand. The optically active bisphosphinomethane is represented by the general formula (1), and the transition metal complex has the optically active bisphosphinomethane as a ligand.

[Formula 1]

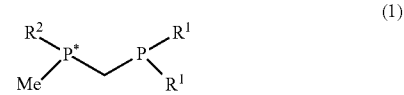

(1)

(In the formula, $R^1$ represents an adamantyl group; $R^2$ represents a branched alkyl group having 3 or more carbon atoms; and * represents an asymmetric center on a phosphorus atom.)

6 Claims, No Drawings

OPTICALLY ACTIVE BISPHOSPHINOMETHANE, METHOD FOR PRODUCING THE SAME, AND TRANSITION METAL COMPLEX AND ASYMMETRIC CATALYST

TECHNICAL FIELD

The present invention relates to a novel bisphosphinomethane derivative and a method for producing the same, and a transition metal complex, an asymmetric catalyst and a method using the catalyst for producing an organic compound.

BACKGROUND ART

Optically active phosphine ligands having an asymmetric center on the phosphorus atom play important roles in catalytic asymmetric synthesis reactions using transition metal complexes. As an optically active phosphine ligand having an asymmetric center on the phosphorus atom, a 1,2-bis (dialkylphosphino)benzene derivative is proposed in Patent Literature 1.

In Patent Literature 2, an optically active 2,3-bis(dialkylphosphino)pyrazine derivative is proposed. This pyrazine derivative has a remarkably high electron withdrawability derived from the pyrazine skeleton, and therefore can highly efficiently carry out a reaction for introducing a phosphorus atom to a heterocycle, which reaction would be generally liable to give a low yield. Further since the phosphorus atom of the pyrazine derivative has a feature of being low in electron density, it is effective that a metal complex having the pyrazine derivative as a ligand is used as a reaction catalyst making the best use of the feature.

Patent Literature 3 and Patent Literature 4 propose an optically active bisphosphincmethane. A transition metal complex having the optically active bisphosphinomethane as a ligand has an excellent asymmetric catalytic ability, but is difficult to handle because it is provided as a liquid or an oil. Also, the transition metal complex has to be handled carefully because the phosphine ligand is easily oxidized in air.

CITATION LIST

Patent Literature

Patent Literature 1: Japanese Patent Laid-Open No. 2000-319288
Patent Literature 2: Japanese Patent Laid-Open No. 2007-56007
Patent Literature 3: Japanese Patent Laid-Open No. 2000-136193
Patent Literature 4: WO2005/087370

SUMMARY OF INVENTION

Technical Problem

An object of the present invention is to provide a novel optically active bisphosphinomethane useful as a ligand for an asymmetric catalyst, excellent in oxidation resistance in air, and easy in handling. The object is also to provide a transition metal complex using, as a ligand, an optically active bisphosphinomethane having excellent asymmetric catalytic ability.

Solution to Problem

In pursuit of research on an optically active bisphosphinomethane, the present inventors have found a novel optically active bisphosphinomethane not susceptible to easy oxidation in air, easy in handling because of the state at room temperature (25° C.) being solid, and useful as a ligand for an asymmetric catalyst, and the finding has led to the completion of the present invention.

A first invention is an optically active bisphosphinomethane represented by the following general formula (1).

[Formula 1]

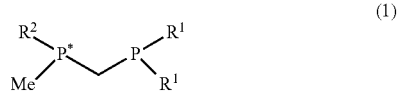

(1)

wherein $R^1$ represents an adamantyl group; $R^2$ represents a branched alkyl group having 3 or more carbon atoms; and * represents an asymmetric center on a phosphorus atom.

A second invention is a method for producing the optically active bisphcsphinomethane of the first invention, comprising:

a first step of preparing a lithiated phosphine borane made by lithiating a phosphine borane represented by the following general formula (2):

[Formula 2]

(2)

wherein $R^1$ represents an adamantyl group, and preparing an optically active phosphine borane derivative represented by the following general formula (4) made by converting a hydroxyl group of an optically active hydroxymethylphosphine borane represented by the following general formula (3) to a leaving functional group:

[Formula 3]

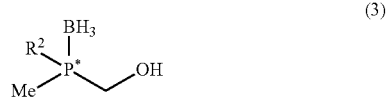

(3)

wherein $R^2$ represents a branched alkyl group having 3 or more carbon atoms; and * represents an asymmetric center on a phosphorus atom.

[Formula 4]

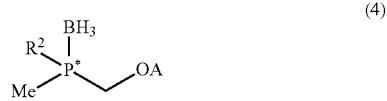

(4)

wherein $R^2$ represents a branched alkyl group having 3 or more carbon atoms; A represents an activated functional group of a hydroxyl group; and * represents an asymmetric center on a phosphorus atom;
  a second step of reacting the lithiated phosphine borane with the optically active phosphine borane derivative represented by the general formula (4) to obtain an optically active bisphosphinomethane borane; and
  a third step of deboranating the optically active bisphosphinomethane borane.

A third invention is a transition metal complex comprising the optically active bisphosphinomethane of the first invention as a ligand.

A fourth invention is an asymmetric catalyst comprising the transition metal complex of the third invention.

Advantageous Effects of Invention

According to the present invention, there can be provided a novel optically active bisphosphinomethane useful as a ligand for an asymmetric catalyst, excellent in oxidation resistance in air, and easy in handling. Further by using, as an asymmetric catalyst, a transition metal complex using the optically active bisphosphinomethane of the present invention as a ligand, the asymmetric catalyst exhibits a high enantio-selectivity and a high reaction activity in an asymmetric hydrogenation reaction, and a target substance can be obtained in a high optical purity and in a high yield.

DESCRIPTION OF EMBODIMENTS

Hereinafter, the present invention will be described based on preferred embodiments.

In the optically active bisphosphinomethane of the present, invention represented by the general formula (1), $R^1$ is an adamantyl group.

With $R^1$ being an adamantyl group, the optically active bisphosphinomethane is solid at room temperature, and in the case where a transition metal complex using this as a ligand is used as an asymmetric catalyst, high enantio-selectivity is exhibited.

$R^2$ of the general formula (1) represents a branched alkyl group having 3 or more carbon atoms. Examples of the branched alkyl group having 3 to more carbon atoms include branched alkyl groups having 3 to 8 carbon atoms such as an isopropyl group, a tert-butyl group and a 1,1,3,3-tetramethylbutyl group (also called "tert-octyl group" in some cases). In the present invention, $R^2$ is preferably a tert-butyl group.

With $R^2$ being a branched alkyl group having 3 or more carbon atoms, in the case where a transition metal complex using the optically active bisphosphincmethane as a ligand is used as an asymmetric catalyst, the transition metal complex exhibits a high reaction activity.

Although conventional optically active bisphosphinomethanes are a liquid or an oil at room temperature, it is also one of features of the present invention that, the optically active bisphosphinomethane of the present invention has a state of being solid at room temperature. Hence, the optically active bisphosphinomethane of the present invention is easy in handling. Further, it is also one of the features that the optically active bisphosphinomethane of the present invention is excellent in oxidation resistance in air. Here, having a state of being solid at room temperature means that the state at 25° C. is being solid.

Hereinafter, a method for producing the optically active bisphosphinomethane represented by the general formula (1) according to the present invention will be described.

The production method of the present invention includes: preparing a lithiated phosphine borane made by lithiating a phosphine borane represented by the general formula (2), and an optically active phosphine borane derivative represented by the general formula (4) made by converting a hydroxyl group of an optically active hydroxymethylphosphine borane represented by the general formula (3) to a leaving functional group; reacting these to obtain an optically active bisphosphinomethane borane; and then deboranating the optically active bisphosphinomethane borane.

That is, the method for producing the optically active bisphosphinomethane represented by the general formula (1) of the present invention comprises the following three steps.

(1) A first step of preparing a lithiated phosphine borane and preparing an optically active phosphine borane derivative
(2) A second step of obtaining an optically active bisphosphinomethane borane
(3) A third step of carrying out a deboranation reaction The first step is a step of preparing a lithiated phosphine borane made by lithiating a phosphine borane represented by the general formula (2), and preparing an optically active phosphine borane derivative represented by the general formula (4) made by converting a hydroxyl group of an optically active hydroxymethylphosphine borane represented by the general formula (3) to a leaving functional group. Here, the order of preparation of these compounds is not especially limited.

The phosphine borane represented by the general formula (2) can be produced by a well-known method. Examples of the production method include methods described in Japanese Patent Laid-Open Nos. 2001-253889, 2003-300988, 2007-70310 and 2010-138136, and J. Org. Chem., 2000, vol. 65, pp. 4135-4188.

The preparation of the lithiated phosphine borane can be carried out by dissolving a phosphine borane represented by the general formula (2) in a solvent, and then adding a lithiating agent thereto to lithiate the phosphine borane represented by the general formula (2).

As the solvent for dissolving the phosphine borane represented by the general formula (2), any solvent can be used without any specific limitations as long as it is a solvent inactive to the phosphine borane represented by the general formula (2) and the lithiated phosphine borane produced by the lithiation of the phosphine borane. Examples of such a solvent include tetrahydrofuran, N,N-dimethylformamide, diethyl ether, tert-butyl methyl ether, cyclopentyl methyl ether, dioxane, hexane and toluene. These solvents can be used singly or as a mixed solvent.

In the preparation of the lithiated phosphine borane, it is preferable, that the concentration of the phosphine borane represented by the general formula (2) in the solvent is 1 to 80% by mass, preferably 5 to 30% by mass, from the viewpoint of the reactivity and the productivity.

As the lithiating agent to be used in the preparation of the lithiated phosphine borane, for example, an organolithium compound is used. The organolithium compound includes methyllithium, ethyllithium, n-propyllithium, sec-propyllithium, n-butyllithium, sec-butyllithium and tert-butyllithium. Among these, n-butyllithium is preferable from the viewpoint of suitable basicity and sufficient reactivity.

From the viewpoint of the economic efficiency and the reactivity, it is preferable that the amount of the lithiating agent to be added is 1.0 to 1.5 equivalents, preferably 1.0 to 1.2 equivalents, with respect to the phosphine borane represented by the general formula (2).

From the viewpoint of the reactivity and the prevention of the side reactions, it is preferable that the temperature of the lithiation is −80° C. to 50° C., preferably −20 to 20° C.

The lithiation is quickly carried out by adding the lithiating agent to a liquid containing the phosphine borane represented by the general formula (2), but in order to complete the reaction of lithiation, as required, after the finish of the addition of the lithiating agent, aging reaction can successively be carried out.

The lithiated phosphine borane is prepared as a solution as described above, and can be used as it is without being isolated, or as required, by being adjusted for the solution concentration, for the second step.

The optically active hydroxymethylphosphine borane represented by the general formula (3) can be produced by a well-known method. Examples of the method include a method in which a dialkylmethylphosphine borane is enantio-selectively deprotonated, and then oxidized (see Japanese Patent Laid-Open No. 2010-209008 or the like).

The preparation of the optically active phosphine borane derivative can be carried out by dissolving the optically active hydroxymethylphosphine borane represented by the general formula (3) in a solvent, and adding a base and an activating agent of a hydroxyl group and being caused to react to convert the hydroxyl group to a leaving functional group.

Examples of the base include triethylamine, tributylamine, diisopropylethylamine, 1,8-diazabicyclo[5.4.0]undec-7-ene, 1,5-diazabicyclo[4.3.0]non-5-ene, methyllithium, ethyllithium, n-propyllithium, sec-propyllithium, n-butyllithium, sec-butyllithium and tert-butyllithium. The amount of the base to be used in the reaction is, with respect to the optically active hydroxyroethylphosphine borane represented by the general formula (3), usually 1 to 3 mol times, and preferably 1 to 2 mol times.

Examples of the activating agent of the hydroxyl group include methanesulfonyl chloride, methanesulfonic anhydride, p-toluenesulfonyl chloride and p-toluenesulfonic anhydride. The amount of the activating agent of the hydroxyl group to be used in the reaction is, with respect to the optically active hydroxymethylphosphine borane represented by the general formula (3), usually 1 to 5 mol times, and preferably 1 to 2 mol times.

The solvent to be used in the reaction is not especially limited as long as it is inactive to the reaction, and examples thereof include tetrahydrofuran, N/N-dimethylformamide, diethyl ether, tert-butyl methyl ether, cyclopentyl methyl ether, dioxane, hexane and toluene. These solvents can be used singly or as a mixed solvent.

The reaction temperature of the reaction is usually −80° C. to 50° C. and preferably −80° C. to 30° C. The reaction time is usually 0.5 hour or longer and preferably 1 to 8 hours.

The optically active phosphine borane derivative represented by the general formula (4) is prepared as a solution as described above, and can be used as it is without being isolated, or as required, by being adjusted for the solution concentration, for the second step.

The second step is a step of reacting the lithiated phosphine borane with the optically active phosphine borane derivative to obtain an optically active bisphosphinoraethane borane represented by the following general formula (5).

[Formula 5]

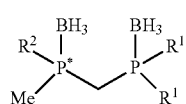

(5)

wherein R$^1$, R$^2$ and * are the same as in the general formula (1).

The reaction can be carried out by mixing a solution of the lithiated phosphine borane prepared in the first step with a solution of the optically active phosphine borane derivative represented by the general formula (4). A mixing method is not especially limited, but it is preferable, because the control of the reaction is easy, that the solution of the lithiated phosphine borane is dropped in and mired with the solution of the optically active phosphine borane derivative.

From the viewpoint of the reactivity and the economic efficiency, it is preferable that the reaction is carried out under the condition that the molar ratio of the lithiated phosphine borane to the optically active phosphine borane derivative represented by the general formula (4) is 0.5 to 3.0, especially 1.0 to 1.5.

From the viewpoint of the reactivity and the prevention of side reactions, it is preferable that the reaction temperature of the reaction is −80 to 50° C., especially −80 to 20° C. The reaction time is usually 0.5 hour or longer and preferably 1 to 8 hours.

After the finish of the reaction, as required, by carrying out purification by a common method such as separatory cleaning, extraction, distillation, desolvation, column chromatography or recrystallization, there can be obtained the optically active bisphosphinomethane borane represented by the general formula (5).

The third step is a step of deboranating the optically active bisphosphinomethane borane represented by the general formula (5) obtained in the second step with a deboranating agent in a solvent to obtain the target optically active bisphosphinomethane represented by the general formula (1).

Examples of the deboranating agent include N,N,N',N'-tetramethylethylenediamine (TMEDA), triethylenediamine, (1,4-diazabicyclo[2.2.2]octane (DABCO), triethylamine, HBF4 and triflucromethanesulfonic acid, but DABCO is preferable.

The amount of the deboranating agent to be added in the deboranation reaction is, with respect to the optically active bisphosphinomethane borane represented by the general formula (5), usually 2 to 10 equivalents and preferably 3 to 5 equivalents.

As the solvent to be used in the reaction, any solvent can be used without any specific limitations as long as it is a solvent capable of dissolving the optically active bisphosphinomethane borane represented by the general formula (5) and inactive to the bisphosphinomethane borane and the optically active bisphosphinomethane represented by the general formula (1) to be produced. Examples thereof include ethyl acetate, tetrahydroxyfuran, N,N-dimethylformamide, diethyl ether, tert-butyl methyl ether, cyclopentyl methyl ether, dioxane, hexane and toluene. These solvents can be used singly or as a mixed solvent.

From the viewpoint of the reaction velocity and the purity of the obtained target substance, it is preferable that the reaction temperature of the deboranation reaction is preferably −20 to 80° C., more preferably 20 to 80° C. The reaction time of the deboranation reaction is preferably 10 min or longer and more preferably 1 to 10 hours.

After the finish of the deboranation reaction, as required, by carrying out purification by a common method such as separatory cleaning, extraction, crystallization, distillation, sublimation, or column chromatography, there can be obtained the target optically active bisphosphinomethane represented by the general formula (1).

The optically active bisphosphinomethane represented by the general formula (1) can form, as a ligand, a complex together with a transition metal. This transition metal complex is useful as an asymmetric synthetic catalyst. Examples of asymmetric synthesis include asymmetric hydrogenation reaction of dehydroamino acids and the like, asymmetric coupling reaction accompanied by C—C bonding or C—N bonding, asymmetric hydrosilylation reaction, asymmetric Tsuji-Trost reaction and asymmetric boronation reaction such as enantio-selective γ-position boron substitution reaction.

In synthesis of organic compounds including a step of carrying out asymmetric reaction by asymmetric catalysts, by using a transition metal complex having the optically active bisphosphinomethane represented by the general formula (1) as a ligand in place of well-known asymmetric catalysts, organic compounds can be produced efficiently such as medicines, agrochemicals, electronic materials and intermediates thereof, in the fields needing optically active substances.

Examples of a transition metal capable of forming a complex with the optically active bisphosphinomethane represented by the general formula (1) include rhodium, ruthenium, iridium, palladium, nickel, iron and copper. Among these, rhodium and palladium are preferable.

A method for forming a complex having the optically active bisphosphinomethane represented by the general formula (1) as a ligand with rhodium metal includes, for example, a method described in Experimental Chemistry Guide Book, 4th edition (edited by The Chemical Society of Japan, published by Maruzen Bookstores Co., vol. 18, pp. 327-353). Specifically, a rhodium complex can be produced by reacting the optically active bisphosphinomethane represented by the general formula (1) with a bis(cyclooctane-1,5-diene)rhodium hexafluoroantimonate salt, a bis(cyclooctane-1,5-diene)rhodium tetrafluoroborate salt or the like.

A method for forming a complex having the optically active bisphosphinomethane represented by the general formula (1) as a ligand with palladium metal includes, for example, a method described in "Y. Uozumi and T. Hayashi, J. Am. Chem. Soc., 1991, 113, 9867". Specifically, a palladium complex can be produced by reacting the optically active bisphosphinomethane represented by the general formula (1) with π-allylpalladium chloride.

The transition metal complex having the optically active bisphosphinomethane represented by the general formula (1) as a ligand can suitably be used as an asymmetric catalyst particularly for asymmetric hydrogenation reaction. A transition metal in this case includes rhodium, ruthenium and iridium. Among these, rhodium is preferable.

Reactions to which the asymmetric catalyst can be applied include reactions using well-known asymmetric hydrogenation catalysts (for example, see Japanese Patent Laid-Open Nos. 2010-208993, 2007-56007, 2000-319288, 2013-6787 and 2012-17288).

EXAMPLES

Hereinafter, the present invention will be described by way of Examples, but the present invention is not any more limited to these Examples.

Synthesis Example 1

(R)-tert-butyl(hydroxymethyl)methyl phosphine borane (3a)

[Formula 6]

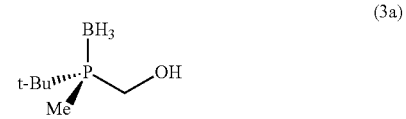

(S)-tert-butylmethylphosphine borane (5.90 g, 50 mmol) and a magnetic stirring bar were put in a 300-mL four-necked flask installed with a three-way cock and a septum, and vacuumizing and argon introduction were several times repeated to replace the system interior by argon. A dehydrated THF (100 mL) was added to dissolve the (S)-tert-butylmethylphosphine borane; thereafter, the solution was cooled to −80° C. and n-BuLi (1.57M hexane solution, 35.0 mL, 55 mmol) was dropped over 5 min. After stirring for 30 min, paraformaldehyde (4.50 g, 150 mmol) was charged at a stroke; and the resultant was heated under vigorous stirring to room temperature over 2 hours. A saturated ammonium chloride aqueous solution (50 mL) was added to stop the reaction; and a resultant mixture was extracted with tert-butyl methyl ether (50 mL×twice). The extract was cleaned with saturated brine, dried with anhydrous sodium sulfate, filtered and vacuum concentrated. A white solid of a residue was purified by silica gel column chromatography (eluate: ethyl acetate/hexane (1:3)) to thereby obtain a target substance as a colorless crystal (6.74 g, yield: 91%). The analysis results are shown below.

mp 182 to 184° C. (decomp.) $[\alpha]D^{27}$−16.5 (c=1.0, AcOEt) Rf=0.37 (AcOEt/hexane (1:3)) $^1$H-NMR (500 MHz, CDCl$_3$) δ 0.05-0.075 (br s, 3H), 1.21 (d, $J_{HP}$=14.4 Hz, 9H), 1.27 (d, $J_{HP}$=10.3 Hz, 3H), 2.02 (br s,1H), 3.95 (d, J=13.2 Hz, 1H), 4.05 (d, J=13.2 Hz, 1H) $^{13}$C-NMR (125 MHz, CDCl$_3$) δ 3.01 (d, $J_{CP}$=34.6 Hz), 25.4, 27.2 (d, $J_{CP}$=32.2 Hz), 57.0 (d, $J_{CP}$=37.0 Hz) $^{31}$P-NMR (202 MHz, CDCl$_3$) δ 28.2

Example 1

According to the following scheme, there was synthesized (R)-di-1-adamantylphosphino(tert-butylmethylphosphino) methane ((R)-BulkyP*).

[Formula 7]

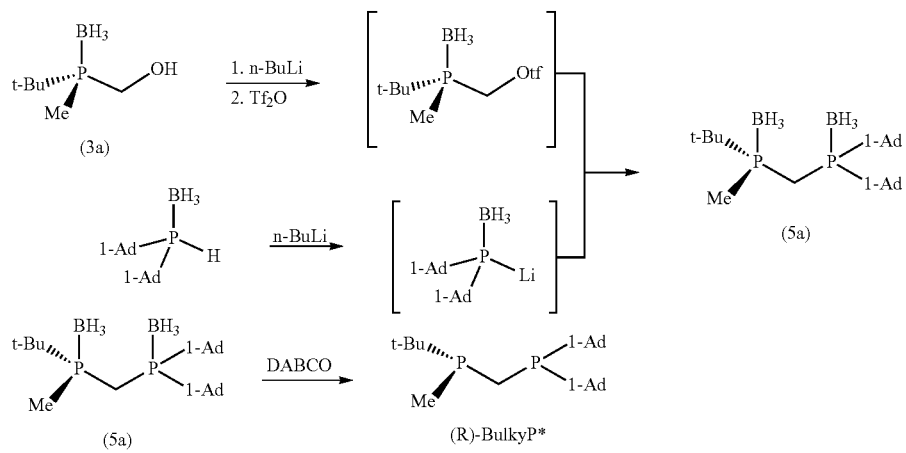

First Step

Di-1-adamantylphosphine borane (1.581 g, 5 mmol) was put in a 50-mL two-necked flask installed with a three-way cock and a septum, and vacuumizing and argon introduction were repeated to replace the system interior by argon. A dehydrated THF (25 mL) was added, and a resultant mixture was cooled to 0° C.; and n-BuLi (1.42 M hexane solution, 3.70 mL, 5.2 mmol) was dropped over 5 min. After the dropping, the resultant was stirred at room temperature for 30 min to thereby obtain a solution (liquid A) of a lithiated substance of di-1-adamantylphosphine borane.

(R)-tert-butyl(methyl)hydroxymethylphosphine borane was put in a 100-mL two-necked flask installed with a three-way cock and a septum, and vacuumizing and argon introduction were repeated to replace the system interior by argon. A dehydrated diethyl ether (10 mL) was added, and the flask was dipped in a low-temperature bath of −80° C.; and n-BuLi (1.42M hexane solution, 3.70 mL, 5.25 mmol) was dropped under stirring by a magnetic stirrer over 5 min. Then, trifluoromethanesulfonic anhydride (0.86 mL, 5.25 mmol) was added by a syringe over about 10 min; and the bath temperature was raised to −30° C. and the stirring was continued for 1 hour to thereby obtain a solution (liquid B) of a trifluoromethanesulfonate ester of (R)-tert-butyl (methyl)hydroxymethylphosphine borane.

Second Step

The two flasks containing the liquid A and the liquid B were connected by a cannula, and the liquid A was dropwise transferred into the flask containing the liquid B over about 20 min. The bath temperature was raised from −30° C. to room temperature over about 2 hours, and the stirring was further continued overnight at the temperature.

The solvent in the reaction mixture was removed by an evaporator; water (20 mL) was added to a resultant residue and well stirred, and thereafter suction filtered by a glass filter (4G). A resultant solid substance was cleaned with water (5 mL×twice) and methanol (3 mL×twice) and vacuum dried to thereby obtain a white powder (1.75 g). This crude product was purified by column chromatography (Wako gel C300, 110 g, dichloromethane/hexane (3:1)) to thereby obtain (R)-boranato(tert-butylmethylphosphino)bo- ranato(di-1-adamantyl)phosphinomethane (5a) (1.20 g, yield: 54%). The analysis results are shown below.

mp ca. 280° C. $[\alpha]_D^{24}$=8.0 (c=1.02, $CDCl_3$) Rf=0.56 (AcOEt/hexane (1:5)) $^1$H-NMR (500 MHz, $CDCl_3$) δ 0.2-1.0 (br m, 6H), 1.23 (d, $^3J_{HP}$=13.8 Hz, 9H), 1.57 (d, $^2J_{HP}$=10.3 Hz, 3H), 1.70-1.80 (m, 12H), 1.82-1.90 (m, 2H), 1.97-2.18 (m, 18H) $^{13}$C-NMR (125 MHz, $CDCl_3$) δ 6.1 (dd, $J_{CP}$=20.9, 14.9 Hz), 6.6 (d, $J_{CP}$32.2 Hz), 25.3, 28.1-28.2 (m), 30.1 (d, $J_{CP}$=35.8 Hz), 36.4, 36.5, 37.6, 37.8, 37.9, 38.9 (d, $J_{CP}$=22.7 Hz) $^{31}$P-NMR (200 MHz, $CDCl_3$) δ 32.6, 40.9

Third Step

The (R)-boranato(tert-butylmethylphosphino) boranato (di-1-adamantyl)phosphinomethane (223 mg, 0.5 mmol) and DABCO (337 mg, 3 mmol) were put in a 10-mL two-necked flask installed with a three-way cock and a septum, and vacuumizing and argon introduction were repeated to replace the system interior by argon. A deaerated toluene (2.5 mL) was added; thereafter, the flask was dipped in an oil bath at 80° C.; and the resultant was caused to react for 3 hours under stirring by a magnetic stirrer. Thereafter, the flask was connected directly to an evaporator and the solvent was removed. Four mL of methanol was added and well stirred for about 10 min; and thereafter, a solid substance was filtered on a 3G glass filter, and cleaned with methanol (3 mL×twice). The resultant was further cleaned with ethyl acetate (2 mL×twice), and thereafter vacuum dried to thereby obtain (R)-di-1-adamantylphosphino(tert-butylmethylphosphino)methane ((R)-BulkyP*) as a white powder (195 mg, yield: 93%). The analysis results are shown below.

mp ca. 265° C. Rf=0.85 (AcOEt/hexane (1:5)) $^1$H-NMR (500 MHZ, $CDCl_3$) δ 1.02 (d, $^2J_{HP}$=3.5 Hz, 3H), 1.06 (d, $^3J_{HP}$=11.5 Hz, 9H), 1, 55-1.62 (m, 2H), 1.66-1.73 (m, 12H), 1.82-1.87 (m, 6H), 1.92-1.99 (m, 12H) $^{13}$C-NMR (125 MHz, $CDCl_3$) δ 7.1 (dd, J=19.5, 6.6 Hz), 11.4 (dd, J=31.0, 22.7 Hz), 26.6 (d, J=13.1 Hz), 28.1 (m), 28.7 (m), 36.2 (m), 36.7 (m), 37.1, 40.9 (d, J=10.7 Hz), 41.3 (dd, J=9.6, 3.6 Hz) $^{31}$P-NMR (202 MHz, $CDCl_3$) δ−13.2 (d, $J_{PP}$=114 Hz), 13.5 (d, $J_{PP}$=114 Hz)

The white powder of (R)-BulkyP* obtained in the above was allowed to stand in air at 25° C. for 24 hours, and thereafter, measurements of $^1$H—, $^{13}$C— and $^{31}$P-NMR were again carried out for confirmation, but no impurities were observed, revealing that (R)-BulkyP* was stable in air.

Example 2

According to the following scheme, a rhodium complex of (R)-BulkyP* was synthesized.

[Formula 8]

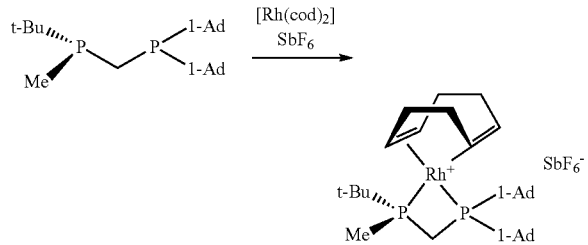

[Rh(cod)$_2$]SbF$_6$ (111 mg, 0.20 mmol) was put in a 20-mL two-necked flask installed with a three-way cock and a septum, and vacuumizing and argon introduction were repeated to replace the system interior by argon, and the resultant was thereafter dissolved by adding a deaerated dichloromethane (6 mL). Separately, (R)-BulkyP* (92 mg, 0.22 mmol) was put in a 10-mL two-necked flask installed with a three-way cock and a septum, and vacuumizing and argon introduction were repeated to replace the system interior by argon, and thereafter, a deaerated THF (2 mL) was added to dissolve (R)-BulkyP*. This solution was extracted by a syringe, and dropped in the dichloromethane solution of [Rh(cod)$_2$]SbF$_6$ prepared in the above under well stirring over about 10 min. After 1 hour, the solvent was removed by an evaporator; and 1.5 mL of ethyl acetate was added to a resultant residue and the content was well mixed by stirring. A deposited orange precipitate was filtered, and cleaned with ethyl acetate (0.5 mL×three times) and vacuum dried (151 mg, 87%).

An obtained product was dissolved in dichloromethane (0.50 mL) in an argon atmosphere; and 2.0 mL of ethyl acetate was added to the resultant solution at a stroke by a syringe. An obtained homogeneous solution was cooled in a refrigerator, and deposited crystals were filtered, and cleaned with a mixed solvent of dichloromethane/ethyl acetate (1:4) and thereafter vacuum dried to thereby obtain orange crystals of a rhodium complex (123 mg, yield: 71%) of (R)-BulkyP*. The analysis results are shown below.

mp 230° C. (decomp.) $^1$H-NMR (500 MHz, CDCl$_3$) δ 1.18 (d, $^3J_{HP}$=15.5 Hz, 9H), 1.71 (d, $^2J_{HP}$=8.6 Hz, 3H), 1.73-2.20 (m, 30H), 2.20-2.33 (m, 4H), 2.38-2.54 (m, 4H), 3.15-3.30 (m, 2H), 5.07 (br s, 1H), 5.11 (br s, 1H), 5.69 (br s, 1H), 5.79 (br s, 1H) $^{13}$C-NMR (125 MHz, CDCl$_3$) δ 9.3 (d, J=20.3 Hz), 25.9 (t, J=18.5 Hz), 26.6 (d, J=3.6 Hz), 28.3 (d, J=8.4 Hz), 28.4 (d, J=8.4 Hz), 28.9, 29.1, 30.9, 31.6, 33.2 (dd, J=17.3, 4.1 Hz), 36.3, 36.4, 40.4, 40.8, 41.3 (d, J=4.8 Hz), 43.4, 91.0 (m), 91.7 (m), 97.4 (m), 100.7 (m) $^{31}$P-NMR (202 MHZ, CDCl$_3$) δ–14.6 (dd, $J_{PP}$=124 HZ, $J_{PRh}$=53 Hz), –30.5 (br d, $J_{PP}$=124 Hz)

Examples 3-1 to 3-12

Asymmetric Hydrogenation Reaction

The rhodium complex (0.005 mmol, 4.3 mg) of (R)-BulkyP* prepared in Example 2, and 0.5 mmol of a substrate represented by the following formula (a1) were charged in a 100-mL pressure-resultant reaction tube. The reaction tube was a stainless steel tube, and connected to a hydrogen gas tank. After the reaction tube was five times replaced by hydrogen gas, a hydrogen gas at 1 atm (manufactured by Japan Fine Products Co., Ltd., 99.99999%) was filled. 3 mL of a degassed methanol was added to the pressure-resistant reaction tube by using a syringe. Then, the pressure of hydrogen gas in the reaction tube was set to 3 atm (in Examples 3 to 5, 1 atm). After hydrogenation reaction was carried out for the reaction time indicated in Table 1 under stirring, hydrogen remaining in the reaction tube was released and the reaction liquid was concentrated by an evaporator to obtain a residue. The residue was purified by flash chromatography (SiC$_2$, ethyl acetate/hexane (3:1)) to obtain a product represented by the formula (a2). The absolute configuration and the ee value of the product were determined from comparison of the retention time with the previously reported value. The results are shown in Table 1.

Then, it was confirmed by each NMR measurement of $^1$H, $^{13}$C and $^{31}$P that, during the reaction, a metal complex was formed in which (R)-BulkyP* was coordinated to a monovalent rhodium ion in 1:1.

[Formula 9]

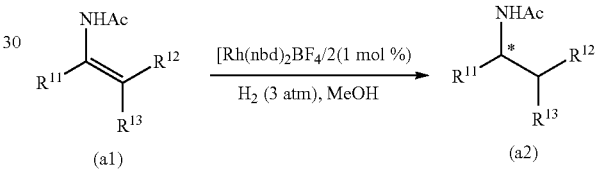

TABLE 1

| | Compounds represented by formulae (a1) and (a2) | | | Reaction time | ee (%) |
|---|---|---|---|---|---|
| Example | R$^{11}$ | R$^{12}$ | R$^{13}$ | (hr) | (configuration) |
| 3-1 | CO$_2$Me | H | H | 0.1 | 99.2 (R) |
| 3-2 | CO$_2$Me | Ph | H | 0.8 | 99.1 (R) |
| 3-3 | CO$_2$Me | Me | Me | 1 | 91.6 (R) |
| 3-4 | Me | H | CO$_2$Me | 0.3 | 99.9 (R) |
| 3-5 | Me | CO$_2$Me | H | 0.8 [1] | 96.5 (R) |
| 3-6 | Ph | CO$_2$Me | H | 3 | 85.1 (S) |
| 3-7 | Ph | H | H | 0.7 | 98.0 (R) |
| 3-8 | 2-Naph | H | H | 0.7 | 98.0 (R) |
| 3-9 | 3-AcOPh | H | H | 0.8 | 97.9 (R) |
| 3-10 | 3,5-(CF$_3$)$_2$Ph | H | H | 0.8 | 96.9 (R) |
| 3-11 | t-Bu | H | H | 0.5 | 97.9 (R |
| 3-12 | 1-Ad | H | H | 0.7 | 95.8 (R) |

[1] Pressure was 1 atm

In formulae, Me is a methyl group; Ph is a phenyl group; Ac is an acetyl group.

Examples 4-1 to 4-3

Asymmetric Hydrogenation Reaction

The rhodium complex (0.005 mmol, 4.3 mg) of (R)-BulkyP* prepared in Example 2, and 0.5 mmol of a substrate represented by the following formula (a3) were charged in a 100-mL pressure-resultant reaction tube, and then subjected to the same procedure as in Examples 3-1 to 3-12 to obtain a product represented by the formula (a4). The absolute configuration and the ee value of the product were determined from comparison of the retention time with the previously reported value. The results are shown in Table 2.

Then, it was confirmed by each NMR measurement of $^1$H, $^{13}$C and $^{31}$P that, during the reaction, a metal complex was formed in which (R)-BulkyP* was coordinated to a monovalent rhodium ion in 1:1.

[Formula 10]

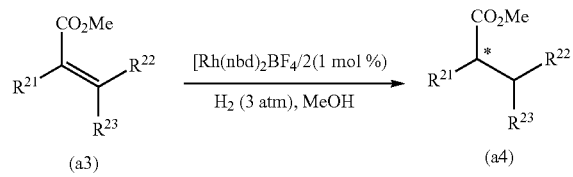

TABLE 2

| Example | Compounds represented by formulae (a3) and (a4) | | | Reaction time (hr) | ee (%) (configuration) |
| --- | --- | --- | --- | --- | --- |
| | $R^{21}$ | $R^{22}$ | $R^{23}$ | | |
| 4-1 | CH$_2$OBn | H | Ph | 0.4 | 99.2 (R) |
| 4-2 | CH$_2$CO$_2$Me | H | H | 0.3 | 99.3 (S) |
| 4-3 | CH$_2$OBn | H | 4-Br-Ph | 1 | 97.8 (R) |

As indicated in Table 1 and Table 2, it is clear that the transition metal complex having the optically active bisphosphinomethane represented by the general formula (1) as a ligand exhibites a high enantio-selectivity in the asymmetric hydrogenation reaction.

The invention claimed is:

1. An optically active bisphosphinomethane having a solid state at 25° C. and represented by the following general formula (1):

[Formula 1]

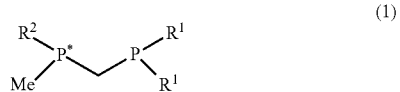

wherein $R^1$ represents an adamantyl group; $R^2$ represents a branched alkyl group having 3 or more carbon atoms; and * represents an asymmetric center on a phosphorus atom.

2. The optically active bisphosphinomethane according to claim 1, wherein $R^2$ in the general formula (1) is a tert-butyl group.

3. A method for producing an optically active bisphosphinomethane according to claim 1, comprising:
a first step of preparing a lithiated phosphine borane made by lithiating a phosphine borane represented by the following general formula (2):

[Formula 2]

wherein $R^1$ represents an adamantyl group, and preparing an optically active phosphine borane derivative represented by the following general formula (4) made by converting a hydroxyl group of an optically active hydroxymethylphosphine borane represented by the following general formula (3) to a leaving functional group:

[Formula 3]

wherein $R^2$ represents a branched alkyl group having 3 or more carbon atoms; and * represents an asymmetric center on a phosphorus atom,

[Formula 4]

wherein $R^2$ represents a branched alkyl group having 3 or more carbon atoms; A represents an activated functional group of a hydroxyl group; and * represents an asymmetric center on a phosphorus atom;
a second step of reacting the lithiated phosphine borane with the optically active phosphine borane derivative represented by the general formula (4) to obtain an optically active bisphosphinomethane borane; and
a third step of deboranating the optically active bisphosphinomethane borane.

4. A transition metal complex, comprising the optically active bisphosphinomethane according to claim 1 as a ligand.

5. An asymmetric catalyst, comprising the transition metal complex according to claim 4.

6. A method for producing an organic compound, comprising a step of carrying out a hydrogenation asymmetric reaction using the asymmetric catalyst according to claim 5, wherein the transition metal complex comprises a metal selected from the group consisting of rhodium, ruthenium or iridium.

* * * * *